United States Patent
Watanabe et al.

(10) Patent No.: US 7,037,995 B2
(45) Date of Patent: May 2, 2006

(54) TERTIARY (METH)ACRYLATES HAVING LACTONE STRUCTURE, POLYMERS, RESIST COMPOSITIONS AND PATTERNING PROCESS

(75) Inventors: Takeru Watanabe, Niigata-ken (JP); Takeshi Kinsho, Niigata-ken (JP); Koji Hasegawa, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 287 days.

(21) Appl. No.: 10/671,791

(22) Filed: Sep. 29, 2003

(65) Prior Publication Data

US 2005/0250924 A1    Nov. 10, 2005

(30) Foreign Application Priority Data

Sep. 30, 2002    (JP) .............................. 2002-285175

(51) Int. Cl.
    *C08F 220/12*    (2006.01)

(52) U.S. Cl. .................. 526/329.6; 526/268; 526/270; 526/281; 526/282; 526/284; 526/320; 549/295; 549/297; 549/300; 430/270.1

(58) Field of Classification Search ................ 526/268, 526/270, 281, 282, 284, 320, 329.6; 549/295, 549/297, 300; 430/270.1
See application file for complete search history.

(56) References Cited

U.S. PATENT DOCUMENTS 6,517,994 B1 * 2/2003 Watanabe ................ 430/270.1
6,639,084 B1 * 10/2003 Maeda et al. ................ 549/266

FOREIGN PATENT DOCUMENTS

| JP | 4-39665 A | 2/1992 |
| JP | 9-95479 A | 4/1997 |
| JP | 9-208554 A | 8/1997 |
| JP | 9-230588 A | 9/1997 |
| JP | 10-10739 A | 1/1998 |

* cited by examiner

*Primary Examiner*—Helen L. Pezzuto
(74) *Attorney, Agent, or Firm*—Birch, Stewart, Kolasch & Birch, LLP

(57) ABSTRACT

Novel tertiary (meth)acrylate compounds having a lactone structure are polymerizable into polymers having improved transparency, especially at the exposure wavelength of an excimer laser and dry etching resistance. Resist compositions comprising the polymers are sensitive to high-energy radiation, have a high resolution, and lend themselves to micropatterning with electron beams or deep-UV rays.

10 Claims, No Drawings

TERTIARY (METH)ACRYLATES HAVING LACTONE STRUCTURE, POLYMERS, RESIST COMPOSITIONS AND PATTERNING PROCESS

This invention relates to (i) a novel (meth)acrylate compound having a lactone structure useful as a monomer for polymerization, (ii) a polymer obtained therefrom, (iii) a resist composition comprising the polymer as a base resin for use in the micropatterning technology, and (iv) a patterning process using the resist composition.

BACKGROUND OF THE INVENTION

While a number of recent efforts are being made to achieve a finer pattern rule in the drive for higher integration and operating speeds in LSI devices, deep-ultraviolet lithography is thought to hold particular promise as the next generation in microfabrication technology. In particular, photolithography using a KrF or ArF excimer laser as the light source is strongly desired to reach the practical level as the micropatterning technique capable of achieving a feature size of 0.3 μm or less.

The resist materials for use in photolithography using light of an excimer laser, especially ArF excimer laser having a wavelength of 193 nm, are, of course, required to have a high transparency to light of that wavelength. In addition, they are required to have an etching resistance sufficient to allow for film thickness reduction, a high sensitivity sufficient to eliminate any extra burden on the expensive optical material, and especially, a high resolution sufficient to form a precise micropattern. To meet these requirements, it is crucial to develop a base resin having a high transparency, rigidity and reactivity. None of the currently available polymers satisfy all of these requirements. Practically acceptable resist materials are not yet available.

Known high transparency resins include copolymers of acrylic or methacrylic acid derivatives (see JP-A 4-39665) and polymers containing in the backbone an alicyclic compound derived from a norbornene derivative (see JP-A 10-10739). All these resins are unsatisfactory. For example, copolymers of acrylic or methacrylic acid derivatives are relatively easy to increase reactivity in that highly reactive monomers can be introduced and acid labile units can be increased as desired, but very difficult to increase rigidity because of their backbone structure. On the other hand, the polymers containing alicyclic compounds in the backbone have rigidity within the acceptable range, but are less reactive with acid than poly(meth)acrylate because of their backbone structure, and difficult to increase reactivity because of the low freedom of polymerization. Additionally, since the backbone is highly hydrophobic, these polymers are less adherent when applied to substrates. Therefore, certain resist compositions which are formulated using these polymers as the base resin fail to withstand etching although they have satisfactory sensitivity and resolution. Some other resist compositions are highly resistant to etching, but have low sensitivity and low resolution below the practically acceptable level.

SUMMARY OF THE INVENTION

An object of the invention is to provide a novel monomer to form a polymer for use in the formulation of a resist composition which is improved in all of adhesion, transparency, etching resistance and resolution when processed by photolithography using light with a wavelength of up to 300 nm, especially ArF excimer laser light as the light source. Another object of the invention is to provide a polymer obtained from the monomer, a resist composition comprising the polymer, and a resist patterning process.

We have found that a (meth)acrylate compound having a lactone structure as represented by formula (1) can be prepared in high yields by a simple method to be described later, that a polymer obtained from this (meth)acrylate compound has high transparency at the exposure wavelength of an excimer laser, and that a resist composition comprising the polymer as a base resin is improved in substrate adhesion, etching resistance and resolution. These advantages are obtained presumably because the lactone moiety, polycyclic structure and tertiary ester structure in the (meth)acrylate compound contribute to firm substrate adhesion, high etching resistance and high resolution, respectively.

In a first aspect, the present invention provides a (meth)acrylate compound having the general formula (1).

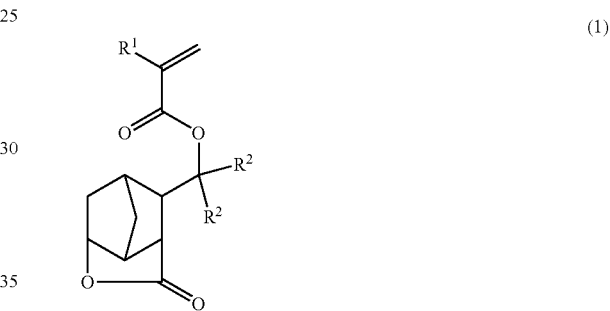

Herein $R^1$ is hydrogen or methyl, and $R^2$ is a straight, branched or cyclic monovalent hydrocarbon group having 1 to 10 carbon atoms, or two $R^2$ may bond together to form a ring with the carbon atom to which they are bonded.

In a second aspect, the present invention provides a polymer comprising recurring units of the general formula (1a) and having a weight average molecular weight of 2,000 to 100,000.

Herein $R^1$ and $R^2$ are as defined above.

In a preferred embodiment, the polymer further comprises recurring units of at least one type having the general formula (2a).

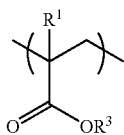

(2a)

Herein $R^1$ is as defined above, and $R^3$ is a tertiary alkyl group of 4 to 20 carbon atoms which may contain a hydroxyl group, carbonyl group, ester bond or ether bond.

In a more preferred embodiment, the polymer further comprises recurring units of at least one type having the general formula (3a).

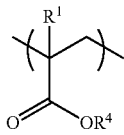

(3a)

Herein $R^1$ is as defined above, and $R^4$ is an alkyl group of 2 to 20 carbon atoms which may contain a hydroxyl group, carbonyl group, ester bond, ether bond or cyano group.

In a third aspect, the present invention provides a resist composition comprising the polymer defined above; preferably a resist composition comprising (A) the polymer defined above, (B) a photoacid generator, (C) an organic solvent, and optionally, (D) a basic compound.

In a fourth aspect, the present invention provides a process for forming a resist pattern comprising the steps of applying the resist composition onto a substrate to form a coating, heat treating the coating and then exposing it to high-energy radiation having a wavelength of up to 300 nm or electron beams through a photomask, and heat treating the exposed coating and developing it with a developer.

DESCRIPTION OF THE PREFERRED EMBODIMENT

The (meth)acrylate compounds having a lactone structure of the present invention have the general formula (1).

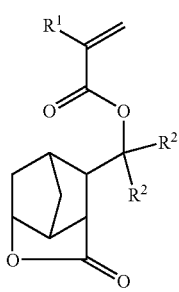

(1)

Herein, $R^1$ is hydrogen or methyl. $R^2$ is a straight, branched or cyclic monovalent hydrocarbon group having 1 to 10 carbon atoms, or two $R^2$ groups may bond together to form a ring with the carbon atom to which they are bonded.

Examples of the straight, branched or cyclic monovalent hydrocarbon group having 1 to 10 carbon atoms represented by $R^2$ include methyl, ethyl, propyl, 2-propyl, butyl, 2-butyl, isobutyl, t-butyl, pentyl, hexyl, cyclohexyl, and decyl. In the event two $R^2$ groups bond together to form a ring, they bond to form an alkylene group of 2 to 20 carbon atoms, especially 2 to 10 carbon atoms, such as ethylene, propylene, trimethylene or tetramethylene. A proper choice of $R^2$ in accordance with an intended application enables to optimize the polarity, ease of acid elimination and other properties of the overall molecule and eventually, the characteristics of a photoresist composition utilizing the inventive compound.

Illustrative examples of the inventive ester compounds are given below although the invention is not limited thereto.

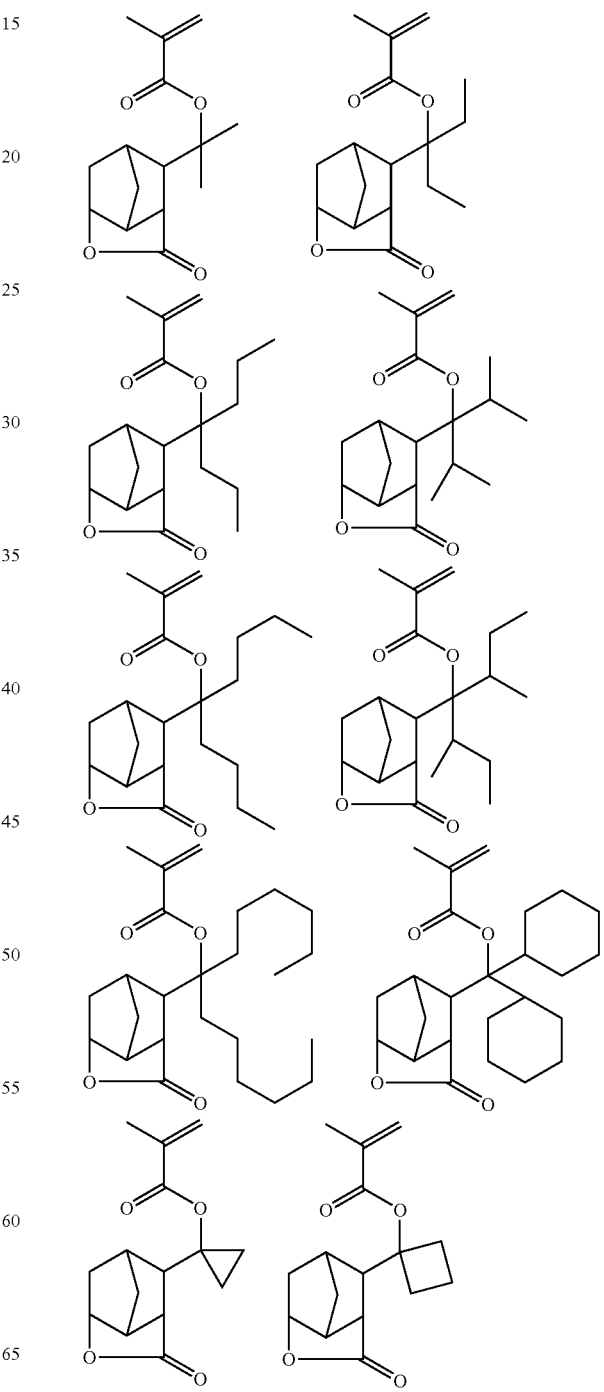

The ester compounds of formula (1) according to the invention can be produced, for example, by the two-step synthesis method to be described below, but the invention is not limited to this method.

A first step of reaction is addition reaction of a metal alkyl, as shown below, namely by adding 2 equivalents of metal alkyl to an ester moiety of a lactone ester compound having formula (4) in a solvent to form a tertiary alcohol compound having formula (5).

Herein, $R^2$ is a straight, branched or cyclic hydrocarbon group having 1 to 10 carbon atoms, and M is Na, K, Li or MgX wherein X is halogen.

Examples of the metal alkyl (RM) used in the addition reaction include methyllithium, methylmagnesium bromide, methylmagnesium chloride, ethylsodium, propylpotassium, isopropylmagnesium iodide, butyllithium, 2-butyllithium, and t-butyllithium. The metal alkyl is preferably used in an amount of 1.5 to 10 moles, more preferably 1.8 to 3 moles per mole of the reactant. If the amount of metal alkyl used is less than 1.5 moles, a large proportion of the reactant may be left unreacted, leading to very low yields. More than 10 moles of the metal alkyl can induce noticeable side reactions, also leading to very low yields.

Examples of the solvent used for the addition reaction include hydrocarbons such as toluene, hexane and heptane, and ethers such as dibutyl ether, diethylene glycol diethyl ether, and tetrahydrofuran. These solvents may be used alone or in admixture.

The temperature for the addition reaction is preferably in the range of about −80° C. to about 50° C. An appropriate reaction temperature may be selected in accordance with other reaction conditions. For example, the optimum temperature is between −80° C. and −60° C. where butyllithium is used as the metal alkyl, and between −40° C. and 10° C. where methylmagnesium bromide is used. Understandably, more side reactions take place as the reaction temperature increases. It is thus important for achieving high yields to perform the reaction at a permissibly lower temperature in the range where reaction proceeds at a practically acceptable rate.

For increased yields, the reaction time is desirably determined by monitoring the progress of reaction by thin-layer chromatography (TLC), gas chromatography (GC) or the like. The reaction time is usually about 30 minutes to about 20 hours.

The reaction is performed in a nitrogen atmosphere by adding a metal alkyl solution to a solution of the reactant or by adding the reactant to a metal alkyl solution. At the end of reaction, a conventional aqueous work-up step gives the target compound (5), tertiary alcohol. If necessary, the target compound (5) is purified by any conventional technique such as recrystallization, chromatography or distillation.

A second step of reaction is the conversion of the tertiary alcohol (5) to the (meth)acrylate ester, as shown below, by conventional methods, for example, a method using (meth) acrylic acid chloride and a base or esterification using (meth)acrylic acid and a dehydrating condensation agent such as dicyclohexylcarbodiimide. If necessary, the (meth) acrylate compound (1) thus obtained is purified by any conventional technique such as chromatography, distillation or recrystallization.

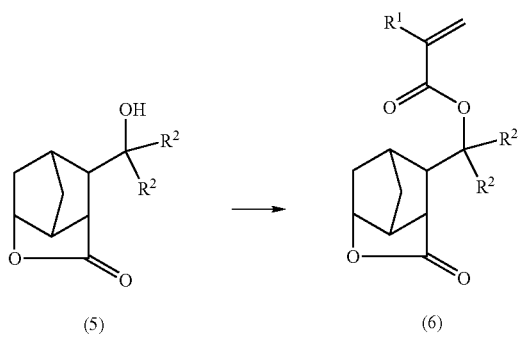

Herein, $R^1$ is hydrogen or methyl, and $R^2$ is a straight, branched or cyclic hydrocarbon group having 1 to 10 carbon atoms.

In the second aspect, the present invention provides a polymer or high molecular weight compound obtained using the ester compound of formula (1) as a monomer. Therefore, the polymer comprises recurring units of the general formula (1a) and has a weight average molecular weight of 2,000 to 100,000.

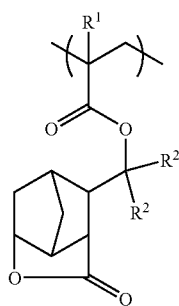

Herein $R^1$ is hydrogen or methyl, and $R^2$ is a straight, branched or cyclic monovalent hydrocarbon group having 1 to 10 carbon atoms, or two $R^2$ may bond together to form a ring with the carbon atom to which they are bonded.

In a preferred embodiment, the polymer further includes recurring units of one or more types having the general formula (2a).

Herein $R^1$ is hydrogen or methyl, and $R^3$ is a tertiary alkyl group of 4 to 20 carbon atoms which may contain a hydroxyl group, carbonyl group, ester bond or ether bond.

In formula (2a), $R^1$ is a hydrogen atom or a methyl group. $R^3$ is a tertiary alkyl group of 4 to 20 carbon atoms which may contain a hydroxyl group, carbonyl group, ester bond or ether bond. Examples of the tertiary alkyl group represented by $R^3$ include, but are not limited to, t-butyl, t-pentyl, 1-ethyl-1-methylpropyl, triethylcarbinyl, 1-methylcyclopentyl, 1-ethylcyclopentyl, 1-cyclopentylcyclopentyl, 1-cyclohexylcyclopentyl, 1-methylcyclohexyl, 1-ethylcyclohexyl, 1-cyclopentylcyclohexyl, 1-cyclohexylcyclohexyl, 2-methyl-2-norbornyl, 2-ethyl-2-norbornyl, 8-methyl-8-tricyclo[5.2.1.0$^{2,6}$]decyl, 8-ethyl-8-tricyclo[5.2.1.0$^{2,6}$]decyl, 3-methyl-3-tetracyclo[4.4.0.1$^{2,5}$.1$^{7,10}$]dodecyl, 3-ethyl-3-tetracyclo[4.4.0.1$^{2,5}$.1$^{7,10}$]dodecyl, 2-methyl-2-adamantyl, 2-ethyl-2-adamantyl, 1-adamantyl-1-methylethyl, 1-methyl-3-oxo-1-cyclohexyl, 1-methyl-1-(tetrahydrofuran-2-yl) ethyl, 5-hydroxy-2-methyl-2-adamantyl, and 5-hydroxy-2-ethyl-2-adamantyl. Specifically, recurring units of formula (2a) are included in a sufficient amount to produce a polymer which is decomposed under the action of an acid to generate a carboxylic acid and turns alkali soluble.

In a more preferred embodiment, the polymer further includes recurring units of one or more types having the general formula (3a) in addition to the recurring units of formulae (1a) and (2a).

Herein $R^1$ is hydrogen or methyl, and $R^4$ is an alkyl group of 2 to 20 carbon atoms which may contain a hydroxyl group, carbonyl group, ester bond, ether bond or cyano group.

In formula (3a), $R^1$ is a hydrogen atom or a methyl group. $R^4$ is an alkyl group of 2 to 20 carbon atoms which may contain a hydroxyl group, carbonyl group, ester bond, ether bond or cyano group. Examples of the alkyl group represented by $R^4$ include, but are not limited to, 2-hydroxyethyl, 2-cyanoethyl, 3-hydroxy-1-adamantyl, 3,5-dihydroxy-1-adamantyl, hydroxynorbornan-2-yl, 3-cyano-1-adamantyl, cyanonorbornan-2-yl, 2-oxo-3-tetrahydrofuranyl, 2-oxo-4-tetrahydrofuranyl, 4-oxa-5-oxotricyclo[5.2.1.0$^{2,6}$]decyl, 2,6-norbornanecarbolacton-3-ylmethyl, 2,6-norbornanecarbolacton-5-yl, 3-methoxycarbonyl-2,6-norbornanecarbolacton-5-yl, and 7-oxa-2,6-norbornanecarbolacton-5-yl. By controlling the type and amount of recurring units of formula (3a) introduced, the polymer is given an optimum balance of hydrophilic and hydrophobic properties.

In addition to the recurring units of formulae (1a), (2a) and (3a), recurring units originating from any of polymerizable compounds having a carbon-to-carbon double bond may be introduced into the inventive polymer for further improving the resist performance. Illustrative examples of such additional compounds are α,β-unsaturated carboxylic acids such as (meth)acrylic acid, α,β-unsaturated carboxylic esters such as (meth)acrylates, crotonates, and maleates, α,β-unsaturated nitriles such as acrylonitrile, α,β-unsaturated lactones such as 5,6-dihydro-2H-pyran-2-one, maleic anhydride, itaconic anhydride, maleimides, norbornene derivatives, tetracyclo[4.4.0.1$^{2,5}$.1$^{7,10}$]dodecene derivatives, allyl ethers, vinyl ethers, vinyl esters, and vinyl silanes.

In the inventive polymer, the recurring units of formula (1a) should preferably be included in a molar fraction of at least 5%, more preferably 10 to 60%, even more preferably 15 to 50%. The recurring units of formula (2a) should preferably be included in a molar fraction of 10 to 70%, more preferably 15 to 65%, even more preferably 20 to 60%; and the recurring units of formula (3a) should preferably be included in a molar fraction of 0 to 60%, more preferably 5 to 55%, even more preferably 10 to 50%.

The polymer of the invention can be prepared by polymerizing the (meth)acrylate compound of formula (1) and the optional polymerizable compounds (to form the above-described additional units) by any conventional technique such as radical, anionic and cationic polymerization techniques.

The polymer of the invention should preferably have a weight average molecular weight (Mw) of about 2,000 to about 100,000. With a Mw of less than 2,000, film formation and resolution may be poor whereas a Mw of more than 100,000 can compromise resolution.

Advantageously, the polymer of the invention is used as a base resin in a resist composition, especially a chemically amplified positive resist composition. Therefore, the present invention in the third aspect provides a resist composition, especially a positive resist composition, comprising the above-described polymer. The resist composition is typically comprised of (A) the above-described polymer as a base resin, (B) a photoacid generator, (C) an organic solvent, and optionally (D) a basic compound.

The photoacid generator (B) may be any compound capable of generating an acid upon exposure to high energy radiation having a wavelength of up to 300 nm or electron beams as long as a resist composition comprising the photoacid generator, the inventive polymer and an organic solvent can be a homogeneous solution which is effectively applicable to form a uniform film.

Examples of the photoacid generator which can be used herein include:
(i) onium salts of the formula (P1a-1), (P1a-2) or (P1b),
(ii) diazomethane derivatives of the formula (P2),
(iii) glyoxime derivatives of the formula (P3),
(iv) bissulfone derivatives of the formula (P4),
(v) sulfonic acid esters of N-hydroxyimide compounds of the formula (P5),
(vi) β-ketosulfonic acid derivatives,
(vii) disulfone derivatives,
(viii) nitrobenzylsulfonate derivatives,
(ix) sulfonate derivatives, and
(x) oxime sulfonates.

These photoacid generators are described in detail.

(i) Onium Salts of Formula (P1a-1), (P1a-2) or (P1b):

Herein, $R^{101a}$, $R^{101b}$, and $R^{101c}$ independently represent straight, branched or cyclic alkyl, alkenyl, oxoalkyl or oxoalkenyl groups of 1 to 12 carbon atoms, aryl groups of 6 to 20 carbon atoms, or aralkyl or aryloxoalkyl groups of 7 to 12 carbon atoms, wherein some or all of the hydrogen atoms may be replaced by alkoxy or other groups. Also, $R^{101b}$ and $R^{101c}$, taken together, may form a ring. $R^{101b}$ and $R^{101c}$ each are alkylene groups of 1 to 6 carbon atoms when they form a ring. K$^-$ is a non-nucleophilic counter ion.

$R^{101a}$, $R^{101b}$, and $R^{101c}$ may be the same or different and are illustrated below. Exemplary alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Exemplary alkenyl groups include vinyl, allyl, propenyl, butenyl, hexenyl, and cyclohexenyl. Exemplary oxoalkyl groups include 2-oxocyclopentyl and 2-oxocyclohexyl as well as 2-oxopropyl, 2-cyclopentyl-2-oxoethyl, 2-cyclohexyl-2-oxoethyl, and 2-(4-methylcyclohexyl)-2-oxoethyl. Exemplary aryl groups include phenyl and naphthyl; alkoxyphenyl groups such as p-methoxyphenyl, m-methoxyphenyl, o-methoxyphenyl, ethoxyphenyl, p-tert-butoxyphenyl, and m-tert-butoxyphenyl; alkylphenyl groups such as 2-methylphenyl, 3-methylphenyl, 4-methylphenyl, ethylphenyl, 4-tert-butylphenyl, 4-butylphenyl, and dimethylphenyl; alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; and dialkoxynaphthyl groups such as dimethoxynaphthyl and diethoxynaphthyl. Exemplary aralkyl groups include benzyl, phenylethyl, and phenethyl. Exemplary aryloxoalkyl groups are 2-aryl-2-oxoethyl groups such as 2-phenyl-2-oxoethyl, 2-(1-naphthyl)-2-oxoethyl, and 2-(2-naphthyl)-2-oxoethyl. Examples of the non-nucleophilic counter ion represented by K$^-$ include halide ions such as chloride and bromide ions, fluoroalkylsulfonate ions such as triflate, 1,1,1-trifluoroethanesulfonate, and nonafluorobutanesulfonate, arylsulfonate ions such as tosylate, benzenesulfonate, 4-fluorobenzenesulfonate, and 1,2,3,4,5-pentafluorobenzenesulfonate, and alkylsulfonate ions such as mesylate and butanesulfonate.

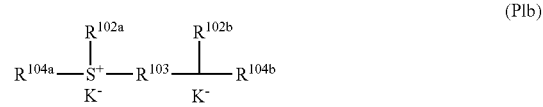

Herein, $R^{102a}$ and $R^{102b}$ independently represent straight, branched or cyclic alkyl groups of 1 to 8 carbon atoms. $R^{103}$ represents a straight, branched or cyclic alkylene groups of 1 to 10 carbon atoms. $R^{104a}$ and $R^{104b}$ independently represent 2-oxoalkyl groups of 3 to 7 carbon atoms. $K^-$ is a non-nucleophilic counter ion.

Illustrative of the groups represented by $R^{102a}$ and $R^{102b}$ are methyl, ethyl, propyl, isopropyl, n-butyl, sec-butyl, tert-butyl, pentyl, hexyl, heptyl, octyl, cyclopentyl, cyclohexyl, cyclopropylmethyl, 4-methylcyclohexyl, and cyclohexylmethyl. Illustrative of the groups represented by $R^{103}$ are methylene, ethylene, propylene, butylene, pentylene, hexylene, heptylene, octylene, nonylene, 1,4-cyclohexylene, 1,2-cyclohexylene, 1,3-cyclopentylene, 1,4-cyclooctylene, and 1,4-cyclohexanedimethylene. Illustrative of the groups represented by $R^{104a}$ and $R^{104b}$ are 2-oxopropyl, 2-oxocyclopentyl, 2-oxocyclohexyl, and 2-oxocycloheptyl. Illustrative examples of the counter ion represented by $K^-$ are the same as exemplified for formulae (P1a-1) and (P1a-2).

(ii) Diazomethane Derivatives of Formula (P2)

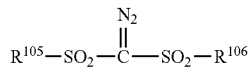

(P2)

Herein, $R^{105}$ and $R^{106}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms.

Of the groups represented by $R^{105}$ and $R^{106}$, exemplary alkyl groups include methyl, ethyl, propyl, isopropyl, n-butyl, sec-butyl, tert-butyl, pentyl, hexyl, heptyl, octyl, amyl, cyclopentyl, cyclohexyl, cycloheptyl, norbornyl, and adamantyl. Exemplary halogenated alkyl groups include trifluoromethyl, 1,1,1-trifluoroethyl, 1,1,1-trichloroethyl, and nonafluorobutyl. Exemplary aryl groups include phenyl; alkoxyphenyl groups such as p-methoxyphenyl, m-methoxyphenyl, o-methoxyphenyl, ethoxyphenyl, p-tert-butoxyphenyl, and m-tert-butoxyphenyl; and alkylphenyl groups such as 2-methylphenyl, 3-methylphenyl, 4-methylphenyl, ethylphenyl, 4-tert-butylphenyl, 4-butylphenyl, and dimethylphenyl. Exemplary halogenated aryl groups include fluorophenyl, chlorophenyl, and 1,2,3,4,5-pentafluorophenyl. Exemplary aralkyl groups include benzyl and phenethyl.

(iii) Glyoxime Derivatives of Formula (P3)

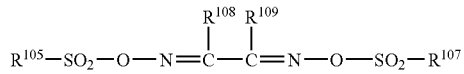

(P3)

Herein, $R^{107}$, $R^{108}$, and $R^{109}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms. Also, $R^{108}$ and $R^{109}$, taken together, may form a ring. $R^{108}$ and $R^{109}$ each are straight or branched alkylene groups of 1 to 6 carbon atoms when they form a ring.

Illustrative examples of the alkyl, halogenated alkyl, aryl, halogenated aryl, and aralkyl groups represented by $R^{107}$, $R^{108}$, and $R^{109}$ are the same as exemplified for $R^{105}$ and $R^{106}$. Examples of the alkylene groups represented by $R^{108}$ and $R^{109}$ include methylene, ethylene, propylene, butylene, and hexylene.

(iv) Bissulfone Derivatives of Formula (P4)

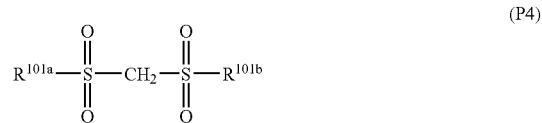

(P4)

Herein, $R^{101a}$ and $R^{101b}$ are as defined above.

(v) Sulfonic Acid Esters of N-hydroxyimide Compounds of Formula (P5)

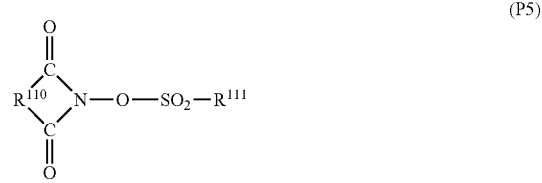

(P5)

Herein, $R^{110}$ is an arylene group of 6 to 10 carbon atoms, alkylene group of 1 to 6 carbon atoms, or alkenylene group of 2 to 6 carbon atoms wherein some or all of the hydrogen atoms may be replaced by straight or branched alkyl or alkoxy groups of 1 to 4 carbon atoms, nitro, acetyl, or phenyl groups. $R^{111}$ is a straight, branched or cyclic alkyl group of 1 to 8 carbon atoms, alkenyl, alkoxyalkyl, phenyl or naphthyl group wherein some or all of the hydrogen atoms may be replaced by alkyl or alkoxy groups of 1 to 4 carbon atoms, phenyl groups (which may have substituted thereon an alkyl or alkoxy of 1 to 4 carbon atoms, nitro, or acetyl group), hetero-aromatic groups of 3 to 5 carbon atoms, or chlorine or fluorine atoms.

Of the groups represented by $R^{110}$, exemplary arylene groups include 1,2-phenylene and 1,8-naphthylene; exemplary alkylene groups include methylene, ethylene, trimethylene, tetramethylene, phenylethylene, and norbornane-2,3-diyl; and exemplary alkenylene groups include 1,2-vinylene, 1-phenyl-1,2-vinylene, and 5-norbornene-2,3-diyl. Of the groups represented by $R^{111}$, exemplary alkyl groups are as exemplified for $R^{101a}$ to $R^{101c}$; exemplary alkenyl groups include vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl, and 7-octenyl; and exemplary alkoxyalkyl groups include methoxymethyl, ethoxymethyl, propoxymethyl, butoxymethyl, pentyloxymethyl, hexyloxymethyl, heptyloxymethyl, methoxyethyl, ethoxyethyl, propoxyethyl, butoxyethyl, pentyloxyethyl, hexyloxyethyl, methoxypropyl, ethoxypropyl, propoxypropyl, butoxypropyl, methoxybutyl, ethoxybutyl, propoxybutyl, methoxypentyl, ethoxypentyl, methoxyhexyl, and methoxyheptyl.

Of the substituents on these groups, the alkyl groups of 1 to 4 carbon atoms include methyl, ethyl, propyl, isopropyl, n-butyl, isobutyl and tert-butyl; and the alkoxy groups of 1 to 4 carbon atoms include methoxy, ethoxy, propoxy, isopropoxy, n-butoxy, isobutoxy, and tert-butoxy. The phenyl groups which may have substituted thereon an alkyl or alkoxy of 1 to 4 carbon atoms, nitro, or acetyl group include phenyl, tolyl, p-tert-butoxyphenyl, p-acetylphenyl and p-nitrophenyl. The hetero-aromatic groups of 3 to 5 carbon atoms include pyridyl and furyl.

Illustrative examples of the photoacid generator include: onium salts such as
diphenyliodonium trifluoromethanesulfonate,
(p-tert-butoxyphenyl)phenyliodonium trifluoromethanesulfonate,
diphenyliodonium p-toluenesulfonate,
(p-tert-butoxyphenyl)phenyliodonium p-toluenesulfonate,
triphenylsulfonium trifluoromethanesulfonate,
(p-tert-butoxyphenyl)diphenylsulfonium trifluoromethanesulfonate,
bis(p-tert-butoxyphenyl)phenylsulfonium trifluoromethanesulfonate,
tris(p-tert-butoxyphenyl)sulfonium trifluoromethanesulfonate,
triphenylsulfonium p-toluenesulfonate,
(p-tert-butoxyphenyl)diphenylsulfonium p-toluenesulfonate,
bis(p-tert-butoxyphenyl)phenylsulfonium p-toluenesulfonate,
tris(p-tert-butoxyphenyl)sulfonium p-toluenesulfonate,
triphenylsulfonium nonafluorobutanesulfonate,
triphenylsulfonium butanesulfonate,
trimethylsulfonium trifluoromethanesulfonate,
trimethylsulfonium p-toluenesulfonate,
cyclohexylmethyl(2-oxocyclohexyl)sulfonium trifluoromethanesulfonate,
cyclohexylmethyl(2-oxocyclohexyl)sulfonium p-toluenesulfonate,
dimethylphenylsulfonium trifluoromethanesulfonate,
dimethylphenylsulfonium p-toluenesulfonate,
dicyclohexylphenylsulfonium trifluoromethanesulfonate,
dicyclohexylphenylsulfonium p-toluenesulfonate,
trinaphthylsulfonium trifluoromethanesulfonate,
cyclohexylmethyl(2-oxocyclohexyl)sulfonium trifluoromethanesulfonate,
(2-norbornyl)methyl(2-oxocyclohexyl)sulfonium trifluoromethanesulfonate,
ethylenebis[methyl(2-oxocyclopentyl)sulfonium trifluoromethanesulfonate], and
1,2'-naphthylcarbonylmethyltetrahydrothiophenium triflate;
diazomethane derivatives such as
bis(benzenesulfonyl)diazomethane,
bis(p-toluenesulfonyl)diazomethane,
bis(xylenesulfonyl)diazomethane,
bis(cyclohexylsulfonyl)diazomethane,
bis(cyclopentylsulfonyl)diazomethane,
bis(n-butylsulfonyl)diazomethane,
bis(isobutylsulfonyl)diazomethane,
bis(sec-butylsulfonyl)diazomethane,
bis(n-propylsulfonyl)diazomethane,
bis(isopropylsulfonyl)diazomethane,
bis(tert-butylsulfonyl)diazomethane,
bis(n-amylsulfonyl)diazomethane,
bis(isoamylsulfonyl)diazomethane,
bis(sec-amylsulfonyl)diazomethane,
bis(tert-amylsulfonyl)diazomethane,
1-cyclohexylsulfonyl-1-(tert-butylsulfonyl)diazomethane,
1-cyclohexylsulfonyl-1-(tert-amylsulfonyl)diazomethane, and
1-tert-amylsulfonyl-1-(tert-butylsulfonyl)diazomethane;
glyoxime derivatives such as
bis-O-(p-toluenesulfonyl)-α-dimethylglyoxime,
bis-O-(p-toluenesulfonyl)-α-diphenylglyoxime,
bis-O-(p-toluenesulfonyl)-α-dicyclohexylglyoxime,
bis-O-(p-toluenesulfonyl)-2,3-pentanedioneglyoxime,
bis-O-(p-toluenesulfonyl)-2-methyl-3,4-pentanedioneglyoxime,
bis-O-(n-butanesulfonyl)-α-dimethylglyoxime,
bis-O-(n-butanesulfonyl)-α-diphenylglyoxime,
bis-O-(n-butanesulfonyl)-α-dicyclohexylglyoxime,
bis-O-(n-butanesulfonyl)-2,3-pentanedioneglyoxime,
bis-O-(n-butanesulfonyl)-2-methyl-3,4-pentanedioneglyoxime,
bis-O-(methanesulfonyl)-α-dimethylglyoxime,
bis-O-(trifluoromethanesulfonyl)-α-dimethylglyoxime,
bis-O-(1,1,1-trifluoroethanesulfonyl)-α-dimethylglyoxime,
bis-O-(tert-butanesulfonyl)-α-dimethylglyoxime,
bis-O-(perfluorooctanesulfonyl)-α-dimethylglyoxime,
bis-O-(cyclohexanesulfonyl)-α-dimethylglyoxime,
bis-O-(benzenesulfonyl)-α-dimethylglyoxime,
bis-O-(p-fluorobenzenesulfonyl)-α-dimethylglyoxime,
bis-O-(p-tert-butylbenzenesulfonyl)-α-dimethylglyoxime,
bis-O-(xylenesulfonyl)-α-dimethylglyoxime, and
bis-O-(camphorsulfonyl)-α-dimethylglyoxime;
bissulfone derivatives such as bisnaphthylsulfonylmethane, bistrifluoromethylsulfonylmethane, bismethylsulfonylmethane, bisethylsulfonylmethane, bispropylsulfonylmethane, bisisopropylsulfonylmethane, bis-p-toluenesulfonylmethane, and bisbenzenesulfonylmethane;
β-ketosulfone derivatives such as 2-cyclohexylcarbonyl-2-(p-toluenesulfonyl)propane and 2-isopropylcarbonyl-2-(p-toluenesulfonyl)propane;
nitrobenzyl sulfonate derivatives such as 2,6-dinitrobenzyl p-toluenesulfonate and 2,4-dinitrobenzyl p-toluenesulfonate;
sulfonic acid ester derivatives such as 1,2,3-tris(methanesulfonyloxy)benzene, 1,2,3-tris(trifluoromethanesulfonyloxy)benzene, and 1,2,3-tris(p-toluenesulfonyloxy)benzene; and
sulfonic acid esters of N-hydroxyimides such as
N-hydroxysuccinimide methanesulfonate,
N-hydroxysuccinimide trifluoromethanesulfonate,
N-hydroxysuccinimide ethanesulfonate,
N-hydroxysuccinimide 1-propanesulfonate,
N-hydroxysuccinimide 2-propanesulfonate,
N-hydroxysuccinimide 1-pentanesulfonate,
N-hydroxysuccinimide 1-octanesulfonate,
N-hydroxysuccinimide p-toluenesulfonate,
N-hydroxysuccinimide p-methoxybenzenesulfonate,
N-hydroxysuccinimide 2-chloroethanesulfonate,
N-hydroxysuccinimide benzenesulfonate,
N-hydroxysuccinimide 2,4,6-trimethylbenzenesulfonate,
N-hydroxysuccinimide 1-naphthalenesulfonate,
N-hydroxysuccinimide 2-naphthalenesulfonate,
N-hydroxy-2-phenylsuccinimide methanesulfonate,
N-hydroxymaleimide methanesulfonate,
N-hydroxymaleimide ethanesulfonate,
N-hydroxy-2-phenylmaleimide methanesulfonate,
N-hydroxyglutarimide methanesulfonate,
N-hydroxyglutarimide benzenesulfonate,
N-hydroxyphthalimide methanesulfonate,
N-hydroxyphthalimide benzenesulfonate,
N-hydroxyphthalimide trifluoromethanesulfonate,
N-hydroxyphthalimide p-toluenesulfonate,
N-hydroxynaphthalimide methanesulfonate,
N-hydroxynaphthalimide benzenesulfonate,
N-hydroxy-5-norbornene-2,3-dicarboxyimide methanesulfonate,
N-hydroxy-5-norbornene-2,3-dicarboxyimide trifluoromethanesulfonate, and N-hydroxy-5-norbornene-2,3-dicarboxyimide p-toluenesulfonate.

Preferred among these photoacid generators are onium salts such as triphenylsulfonium trifluoromethanesulfonate, (p-tert-butoxyphenyl)diphenylsulfonium trifluoromethanesulfonate,
tris(p-tert-butoxyphenyl)sulfonium trifluoromethanesulfonate,
triphenylsulfonium p-toluenesulfonate,
(p-tert-butoxyphenyl)diphenylsulfonium p-toluenesulfonate,
tris(p-tert-butoxyphenyl)sulfonium p-toluenesulfonate,
trinaphthylsulfonium trifluoromethanesulfonate,
cyclohexylmethyl(2-oxocyclohexyl)sulfonium trifluoromethanesulfonate,
(2-norbornyl)methyl(2-oxocylohexyl)sulfonium trifluoromethanesulfonate, and
1,2'-naphthylcarbonylmethyltetrahydrothiophenium triflate;
diazomethane derivatives such as
bis(benzenesulfonyl)diazomethane,
bis(p-toluenesulfonyl)diazomethane,
bis(cyclohexylsulfonyl)diazomethane,
bis(n-butylsulfonyl)diazomethane,
bis(isobutylsulfonyl)diazomethane,
bis(sec-butylsulfonyl)diazomethane,
bis(n-propylsulfonyl)diazomethane,
bis(isopropylsulfonyl)diazomethane, and
bis(tert-butylsulfonyl)diazomethane;
glyoxime derivatives such as
bis-O-(p-toluenesulfonyl)-α-dimethylglyoxime and
bis-O-(n-butanesulfonyl)-α-dimethylglyoxime;
bissulfone derivatives such as bisnaphthylsulfonylmethane;
and sulfonic acid esters of N-hydroxyimide compounds such as
N-hydroxysuccinimide methanesulfonate,
N-hydroxysuccinimide trifluoromethanesulfonate,
N-hydroxysuccinimide 1-propanesulfonate,
N-hydroxysuccinimide 2-propanesulfonate,
N-hydroxysuccinimide 1-pentanesulfonate,
N-hydroxysuccinimide p-toluenesulfonate,
N-hydroxynaphthalimide methanesulfonate, and
N-hydroxynaphthalimide benzenesulfonate.

Also included are the oxime sulfonates described in U.S. Pat. No. 6,004,724, for example, (5-(4-toluenesulfonyl)oxyimino-5H-thiophen-2-ylidene)phenylacetonitrile, (5-(10-camphorsulfonyl)oxyimino-5H-thiophen-2-ylidene)phenylacetonitrile, (5-n-octanesulfonyloxyimino-5H-thiophen-2-ylidene)phenylacetonitrile, (5-(4-toluenesulfonyl)oxyimino-5H-thiophen-2-ylidene) (2-methylphenyl)acetonitrile, (5-(10-camphorsulfonyl)oxyimino-5H-thiophen-2-ylidene) (2-methylphenyl)acetonitrile, (5-n-octanesulfonyloxyimino-5H-thiophen-2-ylidene) (2-methylphenyl)acetonitrile, etc.

Also included are the oxime sulfonates described in U.S. Pat. No. 6,261,738 and JP-A 2000-314956, for example, 2,2,2-trifluoro-1-phenyl-ethanone oxime-O-methylsulfonate; 2,2,2-trifluoro-1-phenyl-ethanone oxime-O-(10-camphoryl-sulfonate); 2,2,2-trifluoro-1-phenyl-ethanone oxime-O-(4-methoxyphenylsulfonate); 2,2,2-trifluoro-1-phenyl-ethanone oxime-O-(1-naphthylsulfonate); 2,2,2-trifluoro-1-phenyl-ethanone oxime-O-(2-naphthylsulfonate); 2,2,2-trifluoro-1-phenyl-ethanone oxime-O-(2,4,6-trimethylphenylsulfonate); 2,2,2-trifluoro-1-(4-methylphenyl)-ethanone oxime-O-(10-camphorylsulfonate); 2,2,2-trifluoro-1-(4-methylphenyl)-ethanone oxime-O-(methylsulfonate); 2,2,2-trifluoro-1-(2-methylphenyl)-ethanone oxime-O-(10-camphorylsulfonate); 2,2,2-trifluoro-1-(2,4-dimethylphenyl)-ethanone oxime-O-(10-camphorylsulfonate); 2,2,2-trifluoro-1-(2,4-dimethylphenyl)-ethanone oxime-O-(1-naphthylsulfonate); 2,2,2-trifluoro-1-(2,4-dimethylphenyl)-ethanone oxime-O-(2-naphthylsulfonate); 2,2,2-trifluoro-1-(2,4,6-trimethylphenyl)-ethanone oxime-O-(10-camphorylsulfonate); 2,2,2-trifluoro-1-(2,4,6-trimethylphenyl)-ethanone oxime-O-(1-naphthylsulfonate); 2,2,2-trifluoro-1-(2,4,6-trimethylphenyl)-ethanone oxime-O-(2-naphthylsulfonate); 2,2,2-trifluoro-1-(4-methoxyphenyl)-ethanone oxime-O-methylsulfonate; 2,2,2-trifluoro-1-(4-methylthiophenyl)-ethanone oxime-O-methylsulfonate; 2,2,2-trifluoro-1-(3,4-dimethoxyphenyl)-ethanone oxime-O-methylsulfonate; 2,2,3,3,4,4,4-heptafluoro-1-phenyl-butanone oxime-O-(10-camphorylsulfonate); 2,2,2-trifluoro-1-(phenyl)-ethanone oxime-O-methylsulfonate; 2,2,2-trifluoro-1-(phenyl)-ethanone oxime-O-10-camphorylsulfonate; 2,2,2-trifluoro-1-(phenyl)-ethanone oxime-O-(4-methoxyphenyl)sulfonate; 2,2,2-trifluoro-1-(phenyl)-ethanone oxime-O-(1-naphthyl)sulfonate; 2,2,2-trifluoro-1-(phenyl)-ethanone oxime-O-(2-naphthyl)sulfonate; 2,2,2-trifluoro-1-(phenyl)-ethanone oxime-O-(2,4,6-trimethylphenyl)sulfonate; 2,2,2-trifluoro-1-(4-methylphenyl)-ethanone oxime-O-(10-camphoryl)sulfonate; 2,2,2-trifluoro-1-(4-methylphenyl)-ethanone oxime-O-methylsulfonate; 2,2,2-trifluoro-1-(2-methylphenyl)-ethanone oxime-O-(10-camphoryl)sulfonate; 2,2,2-trifluoro-1-(2,4-dimethylphenyl)-ethanone oxime-O-(1-naphthyl)sulfonate; 2,2,2-trifluoro-1-(2,4-dimethylphenyl)-ethanone oxime-O-(2-naphthyl)sulfonate; 2,2,2-trifluoro-1-(2,4,6-trimethylphenyl)-ethanone oxime-O-(10-camphoryl)sulfonate; 2,2,2-trifluoro-1-(2,4,6-trimethylphenyl)-ethanone oxime-O-(1-naphthyl)sulfonate; 2,2,2-trifluoro-1-(2,4,6-trimethylphenyl)-ethanone oxime-O-(2-naphthyl)sulfonate; 2,2,2-trifluoro-1-(4-methoxyphenyl)-ethanone oxime-O-methylsulfonate; 2,2,2-trifluoro-1-(4-thiomethylphenyl)-ethanone oxime-O-methylsulfonate; 2,2,2-trifluoro-1-(3,4-dimethoxyphenyl)-ethanone oxime-O-methylsulfonate; 2,2,2-trifluoro-1-(4-methoxyphenyl)-ethanone oxime-O-(4-methylphenyl)sulfonate; 2,2,2-trifluoro-1-(4-methoxyphenyl)-ethanone oxime-O-(4-methoxyphenyl)sulfonate; 2,2,2-trifluoro-1-(4-methoxyphenyl)-ethanone oxime-O-(4-dodecylphenyl)-sulfonate; 2,2,2-trifluoro-1-(4-methoxyphenyl)-ethanone oxime-O-octylsulfonate; 2,2,2-trifluoro-1-(4-thiomethyl-phenyl)-ethanone oxime-O-(4-methoxyphenyl)sulfonate; 2,2,2-trifluoro-1-(4-thiomethylphenyl)-ethanone oxime-O-(4-dodecylphenyl)sulfonate; 2,2,2-trifluoro-1-(4-thiomethylphenyl)-ethanone oxime-O-octylsulfonate; 2,2,2-trifluoro-1-(4-thiomethylphenyl)-ethanone oxime-O-(2-naphthyl)sulfonate; 2,2,2-trifluoro-1-(2-methylphenyl)-ethanone oxime-O-methylsulfonate; 2,2,2-trifluoro-1-(4-methylphenyl)ethanone oxime-O-phenylsulfonate; 2,2,2-trifluoro-1-(4-chlorophenyl)-ethanone oxime-O-phenylsulfonate; 2,2,3,3,4,4,4-heptafluoro-1-(phenyl)-butanone oxime-O-(10-camphoryl)sulfonate; 2,2,2-trifluoro-1-naphthyl-ethanone oxime-O-methylsulfonate; 2,2,2-trifluoro-2-naphthyl-ethanone oxime-O-methylsulfonate; 2,2,2-trifluoro-1-[4-benzylphenyl]-ethanone oxime-O-methylsulfonate; 2,2,2-trifluoro-1-[4-(phenyl-1,4-dioxa-but-1-yl)phenyl]-ethanone oxime-O-methylsulfonate; 2,2,2-trifluoro-1-naphthyl-ethanone oxime-O-propylsulfonate; 2,2,2-trifluoro-2-naphthyl-ethanone oxime-O-propylsulfonate; 2,2,2-trifluoro-1-[4-benzylphenyl]-ethanone oxime-O-propyl-sulfonate; 2,2,2-trifluoro-1-[4-methylsulfonylphenyl]-ethanone oxime-O-propylsulfonate; 1,3-bis[1-(4-phenoxyphenyl)-2,2,2-trifluoroethanone oxime-O-sulfonyl]phenyl; 2,2,2-trifluoro-1-[4-methylsulfonyloxyphenyl]-ethanone oxime-O-propylsulfonate; 2,2,2-trifluoro-1-[4-methylcarbonyloxyphenyl]-ethanone oxime-O-propylsulfonate; 2,2,2-trifluoro-1-[6H,7H-5,8-dioxonaphth-2-yl]-ethanone oxime-O-propylsulfonate; 2,2,2-trifluoro-1-[4-methoxycarbonylmethoxyphenyl]-ethanone oxime-O- propylsulfonate; 2,2,2-trifluoro-1-[4-(methoxycarbonyl)-(4-amino-1-oxa-pent-1-yl)-phenyl]-ethanone oxime-O-propylsulfonate; 2,2,2-trifluoro-1-[3,5-dimethyl-4-ethoxyphenyl]-ethanone oxime-O-propylsulfonate; 2,2,2-trifluoro-1-[4-benzyloxyphenyl]-ethanone oxime-O-propylsulfonate; 2,2,2-trifluoro-1-[2-thiophenyl]-ethanone oxime-O-propylsulfonate; and 2,2,2-trifluoro-1-[1-dioxathiophen-2-yl]-ethanone oxime-O-propylsulfonate.

Also included are the oxime sulfonates described in JP-A 9-95479 and JP-A 9-230588 and the references cited therein, for example, α-(p-toluenesulfonyloxyimino)-phenylacetonitrile,
α-(p-chlorobenzenesulfonyloxyimino)-phenylacetonitrile,
α-(4-nitrobenzenesulfonyloxyimino)-phenylacetonitrile,
α-(4-nitro-2-trifluoromethylbenzenesulfonyloxyimino)-phenylacetonitrile,
α-(benzenesulfonyloxyimino)-4-chlorophenylacetonitrile,
α-(benzenesulfonyloxyimino)-2,4-dichlorophenylacetonitrile,
α-(benzenesulfonyloxyimino)-2,6-dichlorophenylacetonitrile,
α-(benzenesulfonyloxyimino)-4-methoxyphenylacetonitrile,
α-(2-chlorobenzenesulfonyloxyimino)-4-methoxyphenylacetonitrile,
α-(benzenesulfonyloxyimino)-2-thienylacetonitrile,
α-(4-dodecylbenzenesulfonyloxyimino)-phenylacetonitrile,
α-[(4-toluenesulfonyloxyimino)-4-methoxyphenyl]acetonitrile,
α-[(dodecylbenzenesulfonyloxyimino)-4-methoxyphenyl]-acetonitrile,
α-(tosyloxyimino)-3-thienylacetonitrile,
α-(methylsulfonyloxyimino)-1-cyclopentenylacetonitrile,
α-(ethylsulfonyloxyimino)-1-cyclopentenylacetonitrile,
α-(isopropylsulfonyloxyimino)-1-cyclopentenylacetonitrile,
α-(n-butylsulfonyloxyimino)-1-cyclopentenylacetonitrile,
α-(ethylsulfonyloxyimino)-1-cyclohexenylacetonitrile,
α-(isopropylsulfonyloxyimino)-1-cyclohexenylacetonitrile, and
α-(n-butylsulfonyloxyimino)-1-cyclohexenylacetonitrile.

Suitable bisoxime sulfonates include those described in JP-A 9-208554, for example, bis(α-(4-toluenesulfonyloxy)imino)-p-phenylenediacetonitrile,
bis(α-(benzenesulfonyloxy)imino)-p-phenylenediacetonitrile,
bis(α-(methanesulfonyloxy)imino)-p-phenylenediacetonitrile,
bis(α-(butanesulfonyloxy)imino)-p-phenylenediacetonitrile,
bis(α-(10-camphorsulfonyloxy)imino)-p-phenylenediacetonitrile,
bis(α-(4-toluenesulfonyloxy)imino)-p-phenylenediacetonitrile,
bis(α-(trifluoromethanesulfonyloxy)imino)-p-phenylenediacetonitrile,
bis(α-(4-methoxybenzenesulfonyloxy)imino)-p-phenylenediacetonitrile,
bis(α-(4-toluenesulfonyloxy)imino)-m-phenylenediacetonitrile,
bis(α-(benzenesulfonyloxy)imino)-m-phenylenediacetonitrile,
bis(α-(methanesulfonyloxy)imino)-m-phenylenediacetonitrile,
bis(α-(butanesulfonyloxy)imino)-m-phenylenediacetonitrile,
bis(α-(10-camphorsulfonyloxy)imino)-m-phenylenediacetonitrile,
bis(α-(4-toluenesulfonyloxy)imino)-m-phenylenediacetonitrile,
bis(α-(trifluoromethanesulfonyloxy)imino)-m-phenylenediacetonitrile,
bis(α-(4-methoxybenzenesulfonyloxy)imino)-m-phenylenediacetonitrile, etc.

These photoacid generators may be used singly or in combinations of two or more thereof. Onium salts are effective for improving rectangularity, while diazomethane derivatives and glyoxime derivatives are effective for reducing standing waves. The combination of an onium salt with a diazomethane or a glyoxime derivative allows for fine adjustment of the profile.

The photoacid generator is added in an amount of 0.1 to 50 parts, and especially 0.5 to 40 parts by weight, per 100 parts by weight of the base resin (all parts are by weight, hereinafter). Less than 0.1 part of the photoacid generator may generate a less amount of acid upon exposure, sometimes leading to a poor sensitivity and resolution whereas more than 50 parts of the photoacid generator may adversely affect the transmittance and resolution of resist.

The organic solvent (C) used herein may be any organic solvent in which the base resin, photoacid generator, and other components are soluble. Illustrative, non-limiting, examples of the organic solvent include ketones such as cyclohexanone and methyl isopentyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone. These solvents may be used alone or in combinations of two or more thereof. Of the above organic solvents, it is recommended to use diethylene glycol dimethyl ether and 1-ethoxy-2-propanol in which the photoacid generator is most soluble, propylene glycol monomethyl ether acetate, cyclohexanone, or a mixture thereof.

An appropriate amount of the organic solvent used is about 200 to 1,000 parts, especially about 400 to 800 parts by weight per 100 parts by weight of the base resin.

Component (D)

The basic compound used as component (D) is preferably a compound capable of suppressing the rate of diffusion when the acid generated by the photoacid generator diffuses within the resist film. The inclusion of this type of basic compound holds down the rate of acid diffusion within the resist film, resulting in better resolution. In addition, it suppresses changes in sensitivity following exposure and reduces substrate and environment dependence, as well as improving the exposure latitude and the pattern profile.

Examples of basic compounds include primary, secondary, and tertiary aliphatic amines, mixed amines, aromatic amines, heterocyclic amines, carboxyl group-bearing nitrogenous compounds, sulfonyl group-bearing nitrogenous compounds, hydroxyl group-bearing nitrogenous compounds, hydroxyphenyl group-bearing nitrogenous compounds, alcoholic nitrogenous compounds, amide derivatives, and imide derivatives.

Examples of suitable primary aliphatic amines include ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Examples of suitable tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridine, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable carboxyl group-bearing nitrogenous compounds include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Examples of suitable sulfonyl group-bearing nitrogenous compounds include 3-pyridinesulfonic acid and pyridinium p-toluenesulfonate. Examples of suitable hydroxyl group-bearing nitrogenous compounds, hydroxyphenyl group-bearing nitrogenous compounds, and alcoholic nitrogenous compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Examples of suitable amide derivatives include formamide, N-methylformamide, N,N-dimethylformamide, acetamide, N-methylacetamide, N,N-dimethylacetamide, propionamide, and benzamide. Suitable imide derivatives include phthalimide, succinimide, and maleimide.

In addition, basic compounds of the following general formula (B)-1 may also be included alone or in admixture.

$$N(X)_n(Y)_{3-n} \quad (B)\text{-}1$$

In the formula, n is equal to 1, 2 or 3; side chain Y is independently hydrogen or a straight, branched or cyclic alkyl group of 1 to 20 carbon atoms which may contain an ether or hydroxyl group; and side chain X is independently selected from groups of the following general formulas (X)-1 to (X)-3, and two or three X's may bond together to form a ring.

(X)-1

(X)-2

(X)-3

In the formulas, $R^{300}$, $R^{302}$ and $R^{305}$ are independently straight or branched alkylene groups of 1 to 4 carbon atoms; $R^{301}$ and $R^{304}$ are independently hydrogen, straight, branched or cyclic alkyl groups of 1 to 20 carbon atoms, which may contain at least one hydroxyl, ether, ester group or lactone ring; $R^{303}$ is a single bond or a straight or branched alkylene group of 1 to 4 carbon atoms; and $R^{306}$ is a straight, branched or cyclic alkyl groups of 1 to 20 carbon atoms, which may contain at least one hydroxyl, ether, ester group or lactone ring.

Illustrative examples of the basic compounds of formula (B)-1 include tris(2-methoxymethoxyethyl)amine,
tris{2-(2-methoxyethoxy)ethyl}amine,
tris{2-(2-methoxyethoxymethoxy)ethyl}amine,
tris{2-(1-methoxyethoxy)ethyl}amine,
tris{2-(1-ethoxyethoxy)ethyl}amine,
tris{2-(1-ethoxypropoxy)ethyl}amine,
tris[2-{2-(2-hydroxyethoxy)ethoxy}ethyl]amine,
4,7,13,16,21,24-hexaoxa-1,10-diazabicyclo[8.8.8]hexacosane,
4,7,13,18-tetraoxa-1,10-diazabicyclo[8.5.5]eicosane,
1,4,10,13-tetraoxa-7,16-diazabicyclooctadecane,
1-aza-12-crown-4, 1-aza-15-crown-5, 1-aza-18-crown-6,
tris(2-formyloxyethyl)amine, tris(2-acetoxyethyl)amine,
tris(2-propionyloxyethyl)amine, tris(2-butyryloxyethyl)amine,
tris(2-isobutyryloxyethyl)amine, tris(2-valeryloxyethyl)amine,
tris(2-pivaloyloxyethyl)amine,
N,N-bis(2-acetoxyethyl)-2-(acetoxyacetoxy)ethylamine,
tris(2-methoxycarbonyloxyethyl)amine,
tris(2-tert-butoxycarbonyloxyethyl)amine,
tris[2-(2-oxopropoxy)ethyl]amine,
tris[2-(methoxycarbonylmethyl)oxyethyl]amine,
tris[2-(tert-butoxycarbonylmethyloxy)ethyl]amine,
tris[2-(cyclohexyloxycarbonylmethyloxy)ethyl]amine,
tris(2-methoxycarbonylethyl)amine,
tris(2-ethoxycarbonylethyl)amine,
N,N-bis(2-hydroxyethyl)-2-(methoxycarbonyl)ethylamine,
N,N-bis(2-acetoxyethyl)-2-(methoxycarbonyl)ethylamine,
N,N-bis(2-hydroxyethyl)-2-(ethoxycarbonyl)ethylamine,
N,N-bis(2-acetoxyethyl)-2-(ethoxycarbonyl)ethylamine,
N,N-bis(2-hydroxyethyl)-2-(2-methoxyethoxycarbonyl)ethylamine,
N,N-bis(2-acetoxyethyl)-2-(2-methoxyethoxycarbonyl)ethylamine,
N,N-bis(2-hydroxyethyl)-2-(2-hydroxyethoxycarbonyl)ethylamine,
N,N-bis(2-acetoxyethyl)-2-(2-acetoxyethoxycarbonyl)ethylamine,
N,N-bis(2-hydroxyethyl)-2-[(methoxycarbonyl)methoxycarbonyl]ethylamine,
N,N-bis(2-acetoxyethyl)-2-[(methoxycarbonyl)methoxycarbonyl]ethylamine,
N,N-bis(2-hydroxyethyl)-2-(2-oxopropoxycarbonyl)ethylamine,
N,N-bis(2-acetoxyethyl)-2-(2-oxopropoxycarbonyl)ethylamine,
N,N-bis(2-hydroxyethyl)-2-(tetrahydrofurfuryloxycarbonyl)ethylamine,
N,N-bis(2-acetoxyethyl)-2-(tetrahydrofurfuryloxycarbonyl)ethylamine,
N,N-bis(2-hydroxyethyl)-2-[(2-oxotetrahydrofuran-3-yl)oxycarbonyl]ethylamine,
N,N-bis(2-acetoxyethyl)-2-[(2-oxotetrahydrofuran-3-yl)oxycarbonyl]ethylamine,
N,N-bis(2-hydroxyethyl)-2-(4-hydroxybutoxycarbonyl)ethylamine,
N,N-bis(2-formyloxyethyl)-2-(4-formyloxybutoxycarbonyl)ethylamine,
N,N-bis(2-formyloxyethyl)-2-(2-formyloxyethoxycarbonyl)ethylamine,
N,N-bis(2-methoxyethyl)-2-(methoxycarbonyl)ethylamine,
N-(2-hydroxyethyl)-bis[2-(methoxycarbonyl)ethyl]amine,
N-(2-acetoxyethyl)-bis[2-(methoxycarbonyl)ethyl]amine,
N-(2-hydroxyethyl)-bis[2-(ethoxycarbonyl)ethyl]amine,
N-(2-acetoxyethyl)-bis[2-(ethoxycarbonyl)ethyl]amine,
N-(3-hydroxy-1-propyl)-bis[2-(methoxycarbonyl)ethyl]amine,
N-(3-acetoxy-1-propyl)-bis[2-(methoxycarbonyl)ethyl]amine,
N-(2-methoxyethyl)-bis[2-(methoxycarbonyl)ethyl]amine,
N-butyl-bis[2-(methoxycarbonyl)ethyl]amine,
N-butyl-bis[2-(2-methoxyethoxycarbonyl)ethyl]amine,
N-methyl-bis(2-acetoxyethyl)amine,
N-ethyl-bis(2-acetoxyethyl)amine,
N-methyl-bis(2-pivaloyloxyethyl)amine,
N-ethyl-bis[2-(methoxycarbonyloxy)ethyl]amine,
N-ethyl-bis[2-(tert-butoxycarbonyloxy)ethyl]amine,
tris(methoxycarbonylmethyl)amine,
tris(ethoxycarbonylmethyl)amine,
N-butyl-bis(methoxycarbonylmethyl)amine,
N-hexyl-bis(methoxycarbonylmethyl)amine, and
β-(diethylamino)-δ-valerolactone.

Also useful are one or more of cyclic structure-bearing basic compounds having the following general formula (B)-2.

(B)-2

Herein X is as defined above, and $R^{307}$ is a straight or branched alkylene group of 2 to 20 carbon atoms which may contain one or more carbonyl, ether, ester or sulfide groups.

Illustrative examples of the cyclic structure-bearing basic compounds having formula (B)-2 include
1-[2-(methoxymethoxy)ethyl]pyrrolidine,
1-[2-(methoxymethoxy)ethyl]piperidine,
4-[2-(methoxymethoxy)ethyl]morpholine,
1-[2-[(2-methoxyethoxy)methoxy]ethyl]pyrrolidine,
1-[2-[(2-methoxyethoxy)methoxy]ethyl]piperidine,
4-[2-[(2-methoxyethoxy)methoxy]ethyl]morpholine,
2-(1-pyrrolidinyl)ethyl acetate, 2-piperidinoethyl acetate,
2-morpholinoethyl acetate, 2-(1-pyrrolidinyl)ethyl formate,
2-piperidinoethyl propionate,
2-morpholinoethyl acetoxyacetate,
2-(1-pyrrolidinyl)ethyl methoxyacetate,
4-[2-(methoxycarbonyloxy)ethyl]morpholine,
1-[2-(t-butoxycarbonyloxy)ethyl]piperidine,
4-[2-(2-methoxyethoxycarbonyloxy)ethyl]morpholine,
methyl 3-(1-pyrrolidinyl)propionate,
methyl 3-piperidinopropionate, methyl 3-morpholinopropionate,
methyl 3-(thiomorpholino)propionate,
methyl 2-methyl-3-(1-pyrrolidinyl)propionate,
ethyl 3-morpholinopropionate,
methoxycarbonylmethyl 3-piperidinopropionate,
2-hydroxyethyl 3-(1-pyrrolidinyl)propionate,
2-acetoxyethyl 3-morpholinopropionate,
2-oxotetrahydrofuran-3-yl 3-(1-pyrrolidinyl)propionate,
tetrahydrofurfuryl 3-morpholinopropionate,
glycidyl 3-piperidinopropionate,
2-methoxyethyl 3-morpholinopropionate,
2-(2-methoxyethoxy)ethyl 3-(1-pyrrolidinyl)propionate,
butyl 3-morpholinopropionate,
cyclohexyl 3-piperidinopropionate,
α-(1-pyrrolidinyl)methyl-γ-butyrolactone,
β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, and 2-methoxyethyl morpholinoacetate.

Also, one or more of cyano-bearing basic compounds having the following general formulae (B)-3 to (B)-6 may be blended.

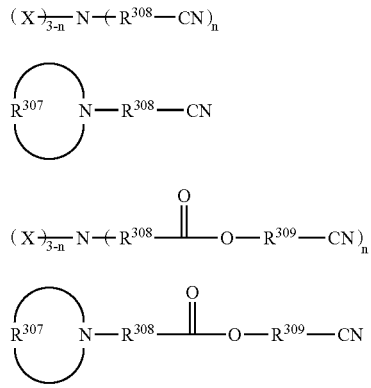

Herein, X, $R^{307}$ and n are as defined above, and $R^{308}$ and $R^{309}$ are each independently a straight or branched alkylene group of 1 to 4 carbon atoms.

Illustrative examples of the cyano-bearing basic compounds having formulae (B)-3 to (B)-6 include
3-(diethylamino)propionitrile,
N,N-bis(2-hydroxyethyl)-3-aminopropiononitrile,
N,N-bis(2-acetoxyethyl)-3-aminopropiononitrile,
N,N-bis(2-formyloxyethyl)-3-aminopropiononitrile,
N,N-bis(2-methoxyethyl)-3-aminopropiononitrile,
N,N-bis[2-(methoxymethoxy)ethyl]-3-aminopropiononitrile,
methyl N-(2-cyanoethyl)-N-(2-methoxyethyl)-3-aminopropionate,
methyl N-(2-cyanoethyl)-N-(2-hydroxyethyl)-3-aminopropionate,
methyl N-(2-acetoxyethyl)-N-(2-cyanoethyl)-3-aminopropionate,
N-(2-cyanoethyl)-N-ethyl-3-aminopropiononitrile,
N-(2-cyanoethyl)-N-(2-hydroxyethyl)-3-aminopropiononitrile,
N-(2-acetoxyethyl)-N-(2-cyanoethyl)-3-aminopropiononitrile,
N-(2-cyanoethyl)-N-(2-formyloxyethyl)-3-aminopropiononitrile,
N-(2-cyanoethyl)-N-(2-methoxyethyl)-3-aminopropiononitrile,
N-(2-cyanoethyl)-N-[2-(methoxymethoxy)ethyl]-3-aminopropiononitrile,
N-(2-cyanoethyl)-N-(3-hydroxy-1-propyl)-3-aminopropiononitrile,
N-(3-acetoxy-1-propyl)-N-(2-cyanoethyl)-3-aminopropiononitrile,
N-(2-cyanoethyl)-N-(3-formyloxy-1-propyl)-3-aminopropiononitrile,
N-(2-cyanoethyl)-N-tetrahydrofurfuryl-3-aminopropiononitrile,
N,N-bis(2-cyanoethyl)-3-aminopropiononitrile,
diethylaminoacetonitrile,
N,N-bis(2-hydroxyethyl)aminoacetonitrile,
N,N-bis(2-acetoxyethyl)aminoacetonitrile,
N,N-bis(2-formyloxyethyl)aminoacetonitrile,
N,N-bis(2-methoxyethyl)aminoacetonitrile,
N,N-bis[2-(methoxymethoxy)ethyl]aminoacetonitrile,
methyl N-cyanomethyl-N-(2-methoxyethyl)-3-aminopropionate,
methyl N-cyanomethyl-N-(2-hydroxyethyl)-3-aminopropionate,
methyl N-(2-acetoxyethyl)-N-cyanomethyl-3-aminopropionate,
N-cyanomethyl-N-(2-hydroxyethyl)aminoacetonitrile,
N-(2-acetoxyethyl)-N-(cyanomethyl)aminoacetonitrile,
N-cyanomethyl-N-(2-formyloxyethyl)aminoacetonitrile,
N-cyanomethyl-N-(2-methoxyethyl)aminoacetonitrile,
N-cyanomethyl-N-[2-(methoxymethoxy)ethyl]aminoacetonitrile,
N-cyanomethyl-N-(3-hydroxy-1-propyl)aminoacetonitrile,
N-(3-acetoxy-1-propyl)-N-(cyanomethyl)aminoacetonitrile,
N-cyanomethyl-N-(3-formyloxy-1-propyl)aminoacetonitrile,
N,N-bis(cyanomethyl)aminoacetonitrile,
1-pyrrolidinepropiononitrile, 1-piperidinepropiononitrile,
4-morpholinepropiononitrile, 1-pyrrolidineacetonitrile,
1-piperidineacetonitrile, 4-morpholineacetonitrile,
cyanomethyl 3-diethylaminopropionate,
cyanomethyl N,N-bis(2-hydroxyethyl)-3-aminopropionate,
cyanomethyl N,N-bis(2-acetoxyethyl)-3-aminopropionate,
cyanomethyl N,N-bis(2-formyloxyethyl)-3-aminopropionate,
cyanomethyl N,N-bis(2-methoxyethyl)-3-aminopropionate,
cyanomethyl N,N-bis[2-(methoxymethoxy)ethyl]-3-aminopropionate,
2-cyanoethyl 3-diethylaminopropionate,
2-cyanoethyl N,N-bis(2-hydroxyethyl)-3-aminopropionate,
2-cyanoethyl N,N-bis(2-acetoxyethyl)-3-aminopropionate,
2-cyanoethyl N,N-bis(2-formyloxyethyl)-3-aminopropionate,
2-cyanoethyl N,N-bis(2-methoxyethyl)-3-aminopropionate,
2-cyanoethyl N,N-bis[2-(methoxymethoxy)ethyl]-3-aminopropionate,
cyanomethyl 1-pyrrolidinepropionate,
cyanomethyl 1-piperidinepropionate,
cyanomethyl 4-morpholinepropionate,
2-cyanoethyl 1-pyrrolidinepropionate,
2-cyanoethyl 1-piperidinepropionate, and
2-cyanoethyl 4-morpholinepropionate.

The basic compounds may be used alone or in admixture of two or more. The basic compound is preferably formulated in an amount of 0.001 to 2 parts, and especially 0.01 to 1 part by weight, per 100 parts by weight of the entire base resin. Less than 0.001 part of the basic compound achieves no or little addition effect whereas more than 2 parts would result in too low a sensitivity.

While the resist composition of the invention is basically composed of the inventive polymer, the photoacid generator, the organic solvent and the basic compound as described above, it may further include any well-known components such as dissolution inhibitors, acidic compounds, stabilizers, dyes, and surfactants, if necessary.

Pattern formation using the resist composition of the invention may be carried out by a known lithographic technique. For example, the resist composition is applied onto a substrate such as a silicon wafer by spin coating or the like to form a resist film having a thickness of 0.3 to 2.0 µm, which is then pre-baked on a hot plate at 60 to 150° C. for 1 to 10 minutes, and preferably at 80 to 130° C. for 1 to 5 minutes. A patterning mask having the desired pattern is then placed over the resist film, and the film exposed through the mask to an electron beam or to high-energy radiation such as deep-UV rays, an excimer laser, or x-rays in a dose of about 1 to 200 mJ/cm$^2$, and preferably about 10 to 100 mJ/cm$^2$, then post-exposure baked (PEB) on a hot plate at 60 to 150° C. for 1 to 5 minutes, and preferably at 80 to 130° C. for 1 to 3 minutes. Finally, development is carried out using as the developer an aqueous alkali solution, such as a 0.1 to 5% (preferably 2 to 3%) aqueous solution of tetramethylammonium hydroxide (TMAH), this being done by a conventional method such as dipping, puddling, or spraying for a period of 0.1 to 3 minutes, and preferably 0.5 to 2 minutes. These steps result in the formation of the desired pattern on the substrate. Of the various types of high-energy radiation that may be used, the resist composition of the invention is best suited to fine pattern formation with, in particular, deep-UV rays having a wavelength of 248 to 193 nm, an excimer laser, x-rays, or an electron beam. The desired pattern may not be obtainable outside the upper and lower limits of the above range.

EXAMPLE

Examples of the invention are given below by way of illustration and not by way of limitation. The meaning of abbreviations is THF for tetrahydrofuran, IR for infrared spectroscopy, NMR for nuclear magnetic resonance, and GPC for gel permeation chromatography.

Example 1

Synthesis of 3-(1-methacryloyloxy-1-methylethyl)-2,6-norbornanecarbolactone (i.e., methacrylate of formula (1) wherein R$^1$=R$^2$=methyl)

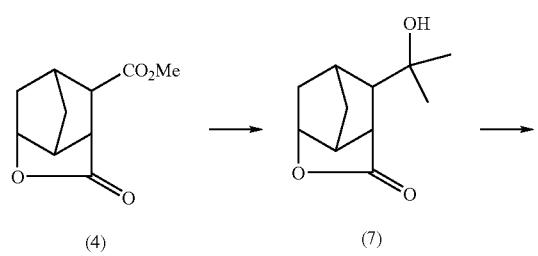

(4)    (7)

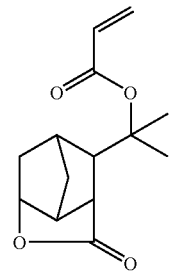

(8)

With stirring in nitrogen and at 0° C., a THF solution of 860 mmol methylmagnesium chloride was added to a solution of 80 g methyl 2,6-norbornanecarbolactone-3-carboxylate of formula (4) in 500 ml THF. The solution was stirred for one hour. An aqueous solution of ammonium chloride was added to stop the reaction, followed by conventional aqueous work-up. The solvent was distilled off in vacuo, yielding 3-(1-hydroxy-1-methylethyl)-2,6-norbornanecarbolactone of formula (7).

Next, to a mixture of the thus obtained 3-(1-hydroxy-1-methylethyl)-2,6-norbornanecarbolactone, 70 g of triethylamine and 400 g of dichloromethane, under ice cooling and with stirring, 55 g of methacryloyl chloride was added. The solution was stirred at room temperature for 12 hours. Water was added to stop the reaction, followed by conventional aqueous work-up. The solvent was distilled off in vacuo. The solid residue was washed with hexane and dried in vacuo, obtaining 86 g of 3-(1-methacryloyloxy-1-methylethyl)-2, 6-norbornanecarbolactone of formula (8). The yield was 80% based on the methyl 2,6-norbornanecarbolactone-3-carboxylate.

IR (KBr): ν=2971, 2960, 2951, 1763, 1711, 1637, 1463, 1450, 1388, 1373, 1331, 1311, 1273, 1203, 1167, 1144, 1126, 1115, 1049, 1012, 968, 957, 945 cm$^{-1}$ $^1$H-NMR (270 MHz in CDCl$_3$): δ=1.32 (3H, s), 1.50 (1H, m), 1.54 (3H, s), 1.65–1.80 (2H, m), 1.90 (3H, m), 2.20 (1H, m), 2.45 (1H, m), 2.53 (1H, m), 3.05–3.15 (2H, m), 5.03 (1H, m), 5.57 (1H, m), 6.17 (1H, m)

Example 2

Synthesis of 3-(1-acryloyloxy-1-methylethyl)-2,6-norbornanecarbolactone (i.e., acrylate of formula (1) wherein R$^1$=hydrogen, R$^2$=methyl)

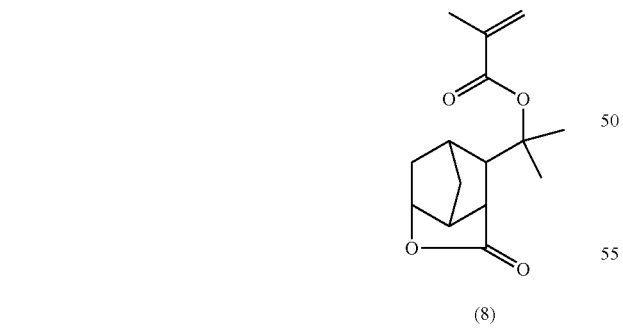

(9)

By following the same procedure as in Example 1 except that 50 g of acryloyl chloride was used instead of the methacryloyl chloride, 3-(1-acryloyloxy-1-methylethyl)-2, 6-norbornanecarbolactone of formula (9) was synthesized. The yield of compound (9) was 76% based on the methyl 2,6-norbornanecarbolactone-3-carboxylate.

Example 3

Synthesis of a polymer having the structural formula (10) wherein x=z=0.35, y=0.30

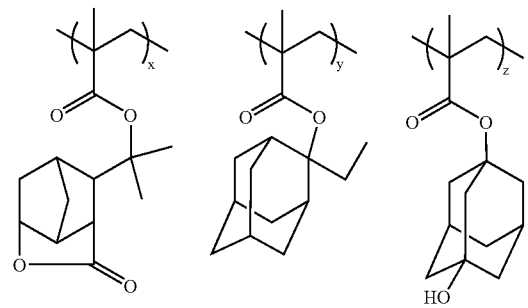

(10)

In a nitrogen atmosphere, a mixture of 9.2 g of the methacrylate (8) obtained in Example 1, 7.4 g of 2-ethyl- 2-adamantyl methacrylate, 8.3 g of 3-hydroxy-1-adamantyl methacrylate, 60 mg of N,N'-azobisisobutyronitrile, and 80 ml of THF was heated and stirred at 60° C. for 20 hours. After cooling, the reaction mixture was added dropwise to 2 liters of methanol under vigorous stirring. The precipitate which settled down was collected by filtration. The solids were washed with methanol and dried in vacuo, obtaining 19.9 g of the desired polymer. The yield was 80%. An integration ratio calculated from its $^1$H-NMR spectrum indicated a copolymerization ratio of approximately 35:30:35. GPC analysis using polystyrene standards indicated a weight average molecular weight (Mw) of 9,800 and a polydispersity index (Mw/Mn) of 1.80.

Example 4

Resist Pattern Formation Using Polymer

Using the polymer obtained in Example 3, a resist material was prepared. Its composition was:
(A) 80 parts by weight of the polymer of Example 3 as a base polymer,
(B) 1.0 part by weight of triphenylsulfonium trifluoromethanesulfonate as a photoacid generator,
(C) 480 parts by weight of propylene glycol monomethyl ether acetate as a solvent, and
(D) 0.08 part by weight of tributylamine as a basic compound.

This was passed through a Teflon® filter having a pore diameter of 0.2 μm. The resist solution was spin coated on a silicon wafer having hexamethyldisilazane sprayed thereon at 90° C. for 40 seconds and heat treated at 110° C. for 90 seconds, forming a resist film of 500 nm thick. The resist film was exposed to ArF excimer laser light, heat treated at 110° C. for 90 seconds, cooled down to 23° C., and dipped in a 2.38% tetramethylammonium hydroxide aqueous solution at 23° C. for 60 seconds for development, thereby forming a 1:1 line-and-space pattern. The wafer as developed was observed under Top-do SEM. Patterns down to a line width of 0.13 μm were left unstripped and hence, resolved. This demonstrates that the photoresist material of the invention has improved substrate adhesion and resolution.

Example 5

Transparency of Polymer

The polymer obtained in Example 3, 1.0 g, was dissolved in 6.0 g of cyclohexanone, which was passed through a Teflon® filter having a pore diameter of 0.2 μm. The solution was spin coated on a quartz substrate and heat treated at 90° C. for 60 seconds, forming a thin film of 500 nm thick. The thin film was measured for transmittance at 193 nm using a UV-visible spectrophotometer, finding a transmittance of 78% per 500 nm thickness. This result demonstrates that the polymer of the invention has a sufficient transparency as the photoresist base polymer for excimer laser photolithography.

Example 6

Etching Resistance of Polymer

The polymer obtained in Example 3, 2 g, was dissolved in 10 g of cyclohexanone, which was passed through a Teflon® filter having a pore diameter of 0.2 μm. The solution was spin coated on a silicon wafer and heat treated at 90° C. for 60 seconds, forming a thin film of 700 nm thick. Using a reactive ion etching apparatus, the thin film was etched with $CF_4$ gas under conditions: power 100 W, pressure 5 Pa, and gas flow rate 30 ml/min. As a result, the etching rate was 1.10 based on a rate of 1.00 normalized for novolac resist. For comparison purposes, the same test was done on poly (p-hydroxystyrene) used as the base polymer for KrF resist, finding an etching rate of 1.20. These results demonstrate that the inventive polymer has a slower etching rate with $CF_4$ gas, that is, better dry etching resistance.

There have been described tertiary (meth)acrylate compounds having a lactone structure which are very advantageous as monomers to base polymers in improving both the resolution and etching resistance of resists. The polymers obtained therefrom have improved transparency, especially at the exposure wavelength of an excimer laser and dry etching resistance. Resist compositions comprising the inventive polymers are sensitive to high-energy radiation, have a high resolution, and lend themselves to micropatterning with electron beams or deep-UV rays. Especially because of firm adhesion to the substrate, finely defined patterns having sidewalls perpendicular to the substrate can easily be formed. The resist compositions are thus suitable as micropatterning material for VLSI fabrication.

Japanese Patent Application No. 2002-285175 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A (meth)acrylate compound having the general formula (1):

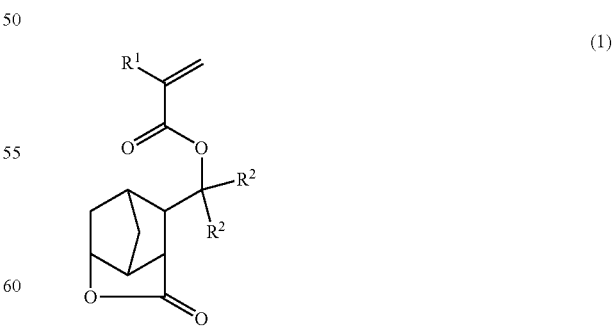

(1)

wherein $R^1$ is hydrogen or methyl, and $R^2$ is a straight, branched or cyclic monovalent hydrocarbon group having 1 to 10 carbon atoms, or two $R^2$ may bond together to form a ring with the carbon atom to which they are bonded.

2. A polymer comprising recurring units of the general formula (1a) and having a weight average molecular weight of 2,000 to 100,000,

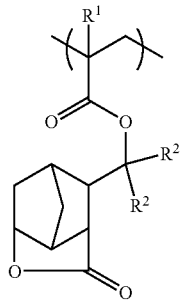
(1a)

wherein $R^1$ is hydrogen or methyl, and $R^2$ is a straight, branched or cyclic monovalent hydrocarbon group having 1 to 10 carbon atoms, or two $R^2$ may bond together to form a ring with the carbon atom to which they are bonded.

3. The polymer of claim 2, further comprising recurring units of at least one type having the general formula (2a):

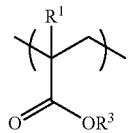
(2a)

wherein $R^1$ is hydrogen or methyl, and $R^3$ is a tertiary alkyl group of 4 to 20 carbon atoms which may contain a hydroxyl group, carbonyl group, ester bond or ether bond.

4. The polymer of claim 3, further comprising recurring units of at least one type having the general formula (3a):

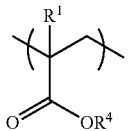
(3a)

wherein $R^1$ is hydrogen or methyl, and $R^4$ is an alkyl group of 2 to 20 carbon atoms which may contain a hydroxyl group, carbonyl group, ester bond, ether bond or cyano group.

5. The polymer of claim 2 wherein the recurring units of formula (1a) are present in a molar fraction of at least 5%.

6. A resist composition comprising the polymer of claim 2.

7. A resist composition comprising
(A) the polymer of claim 2,
(B) a photoacid generator, and
(C) an organic solvent.

8. A resist composition comprising
(A) the polymer of claim 2,
(B) a photoacid generator,
(C) an organic solvent, and
(D) a basic compound.

9. A process for forming a resist pattern comprising the steps of:
applying the resist composition of claim 6 onto a substrate to form a coating,
heat treating the coating and then exposing it to high-energy radiation having a wavelength of up to 300 nm or electron beams through a photomask, and
heat treating the exposed coating and developing it with a developer.

10. 3-(1-methacryloyloxy-1-methylethyl)-2,6-norbornane carbolactone.

* * * * *